United States Patent
Kilpinen et al.

(10) Patent No.: US 9,020,934 B2
(45) Date of Patent: Apr. 28, 2015

(54) METHOD, AN ARRANGEMENT AND A COMPUTER PROGRAM PRODUCT FOR ANALYSING A BIOLOGICAL OR MEDICAL SAMPLE

(75) Inventors: Sami Kilpinen, Helsinki (FI); Kalle Ojala, Helsinki (FI); Timo Ahopelto, Helsinki (FI); Tommi Pisto, Piikkiö (FI)

(73) Assignee: Medisapiens Oy, Helsinki (FI)

( * ) Notice: Subject to any disclaimer, the term of this patent is extended or adjusted under 35 U.S.C. 154(b) by 202 days.

(21) Appl. No.: 13/583,138

(22) PCT Filed: Mar. 11, 2011

(86) PCT No.: PCT/FI2011/050216
§ 371 (c)(1),
(2), (4) Date: Nov. 14, 2012

(87) PCT Pub. No.: WO2011/110751
PCT Pub. Date: Sep. 15, 2011

(65) Prior Publication Data
US 2013/0066860 A1    Mar. 14, 2013

Related U.S. Application Data

(60) Provisional application No. 61/313,207, filed on Mar. 12, 2010.

(30) Foreign Application Priority Data

Mar. 12, 2010   (FI) .................................... 20105252

(51) Int. Cl.
G06F 7/00    (2006.01)
G06F 17/30   (2006.01)
(Continued)

(52) U.S. Cl.
CPC ............... *G06F 19/24* (2013.01); *G06F 19/20* (2013.01); *G06F 19/28* (2013.01); *Y10S 707/941* (2013.01)

(58) Field of Classification Search
USPC .................................. 707/723, 941; 435/6.11
See application file for complete search history.

(56) References Cited

U.S. PATENT DOCUMENTS

2003/0225526 A1* 12/2003 Golub et al. .................... 702/19
2006/0265138 A1* 11/2006 Bowtell et al. .................. 702/20
(Continued)

FOREIGN PATENT DOCUMENTS

WO    03/041562 A2    5/2003
WO    2004/081564 A1  9/2004
(Continued)

OTHER PUBLICATIONS

Finland Office Action in corresponding Finland Application No. 20105252 dated Nov. 26, 2010.
(Continued)

*Primary Examiner* — Greta Robinson
*Assistant Examiner* — Brian E. Weinrich
(74) *Attorney, Agent, or Firm* — Patent Portfolio Builders PLLC

(57) ABSTRACT

An aspect of the present invention is a computer executable method for characterizing, e.g. for diagnostic purposes, utilizing a reference database, a query sample tissue based on the gene expression data of the tissue. The method is characterized in that it comprises the steps of calculating an expression match score (EM-score) indicating the likelihood of having the gene expression level observed in the query sample in each of the tissue categories of the reference database, calculating for the genes of the sample tissue, using e.g. the EM-score, tissue specificity score (TS-score), that expresses how uniquely a gene identifies the query sample as belonging to a certain tissue category, calculating, utilizing e.g. the TS-score, overall similarity of the sample tissue in relation to a tissue category of the reference database, and storing at least some resulting characterization data to a memory device or outputting the data to an output device of a computer. An arrangement and a computer program product are also disclosed.

10 Claims, 4 Drawing Sheets

Figure 1A:
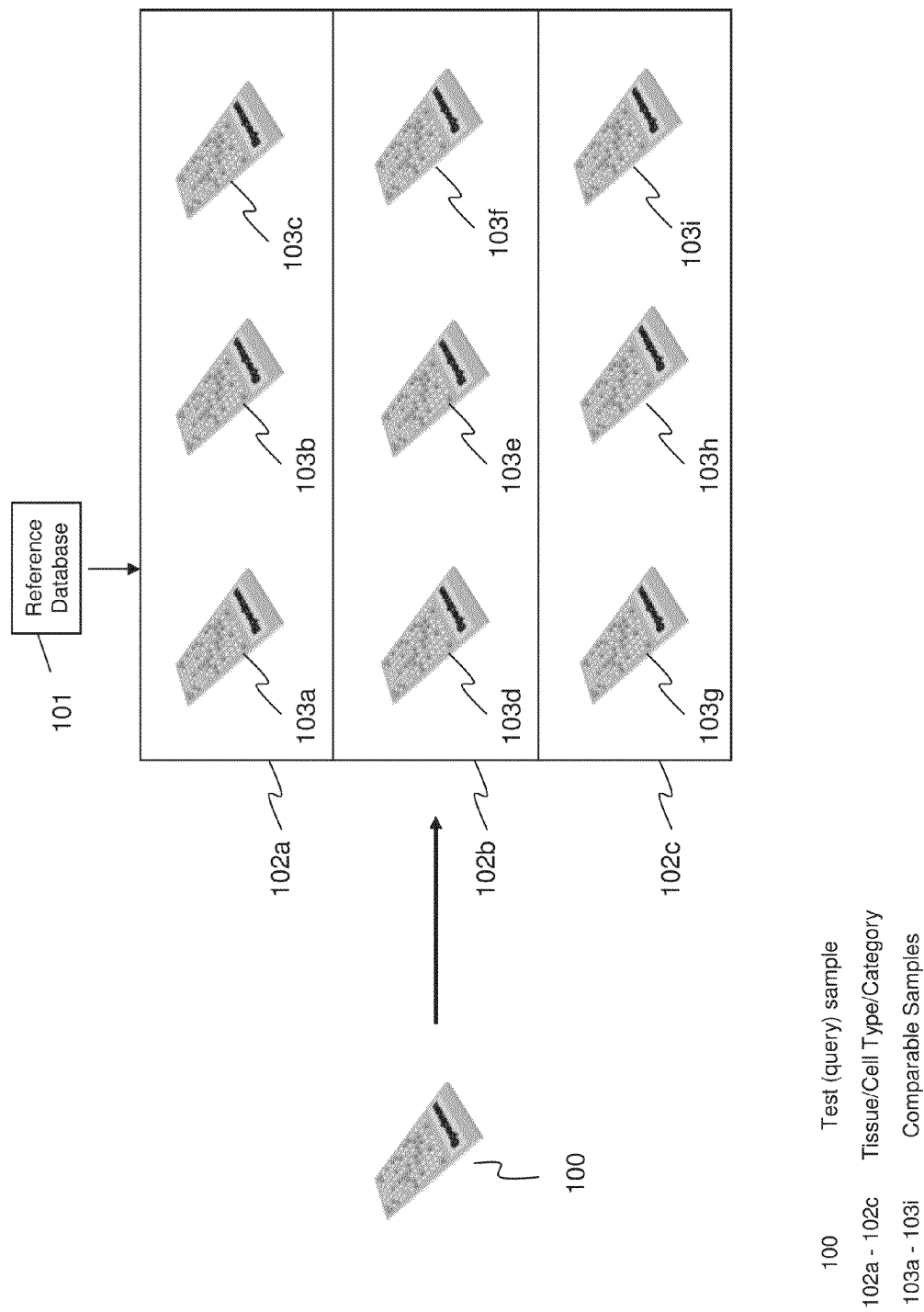

(51) Int. Cl.
*C12Q 1/68* (2006.01)
*G06F 19/24* (2011.01)
*G06F 19/20* (2011.01)
G06F 15/16 (2006.01)
G06F 19/28 (2011.01)

(56) References Cited

U.S. PATENT DOCUMENTS

2010/0094795 A1* 4/2010 Irizarry et al. .......... 706/52
2011/0035159 A1* 2/2011 Kilpinen et al. ......... 702/19

FOREIGN PATENT DOCUMENTS

WO 2008/066596 A2 6/2008
WO 2009/067655 A2 5/2009
WO 2009/125065 A1 10/2009

OTHER PUBLICATIONS

Zilliox, Michael J. et al., "A Gene Expression Bar Code for Micrarray Data", Nature Methods, vol. 4, No. 11, pp. 911-913, Nov. 2007, DOI:10.1038.

International Search Report issued in corresponding International application No. PCT/FI2011/050216, mailing date Jun. 15, 2011.

International Preliminary Report on Patentability issued in corresponding International application No. PCT/FI2011/050216, on Sep. 18, 2012.

* cited by examiner

200 ADIPOQ gene expression range
201 Adipose tissue specific expression range

METHOD, AN ARRANGEMENT AND A COMPUTER PROGRAM PRODUCT FOR ANALYSING A BIOLOGICAL OR MEDICAL SAMPLE

AREA OF INVENTION

The invention relates to the area of bioinformatics. More specifically, the invention relates to analysis method of genetic data for e.g. cancer diagnostics purposes.

BACKGROUND OF THE INVENTION

A large number of methods have been developed for the analysis of microarray gene expression data. This reflects the tremendous complexity of the problem of transforming digital information on expression levels of over 20,000 genes into meaningful biological insights. Many microarray data analysis approaches are based on a case-control study design, for example comparing treated and untreated cells or matched disease and control tissues. In other cases, characteristic subsets of genes or classifiers are built and tested for specific purposes, such as the differential diagnosis of diseases. In most cases, significant numbers of samples from the case and control groups are expected in order to arrive at statistically significant interpretation of differentially expressed genes. Interpretation of data from individual samples is often not possible with these approaches. For example, samples from disease tissues, such as tumors, are often readily available, whereas the corresponding normal tissue samples may be much harder to obtain. In other cases, an appropriate control group is hard to define and challenging to acquire, particularly from human tissues. For example in studies of stem cells, their differentiation patterns should be followed up in comparison to multiple differentiated cell and tissue types to provide a comprehensive understanding of the differentiation patterns of the cells.

Recently, there have been major efforts to develop large-scale databases from publicly available microarray datasets (e.g. GeneSapiens, Oncomine, connectivity map, gene expression omnibus, Array-express) in order to analyze and mine the enormous quantities of microarray data that have been published by the biomedical community. Indeed, analyses of such metadata are increasingly recognized as a powerful means to study gene networks and gene regulation, and to identify tissue- or disease-specific gene expression patterns. Availability of these microarray databases would also provide an opportunity to use a comprehensive collection of reference samples as a means of guiding the interpretation of new microarray data produced by investigators from test samples. This is particularly appealing for the analysis and interpretation of data from individual samples. However, currently there are no tools available for such comparisons. Therefore, the microarray data analysis community would need a tool similar to the simple, yet highly powerful and versatile sequence comparison program (BLAST) [Altschul et al., Basic local alignment search tool, J Mol Biol, 1990] program for matching an unknown test DNA sequence against a comprehensive reference database of previously sequenced samples.

Today, the amount of genetic information increases rapidly including both DNA sequence and functional gene expression genetics. Especially this is the situation in oncology: cancer is a genetic disease on a cellular level, and should be treated and diagnosed as such.

Very large number of publications exists featuring various methods for classifying gene expression profiles to a priori defined classes. Just for the sake of clarification, these are usually divided in two classes. Unsupervised and supervised clustering methods, former is more commonly known as clustering whereas latter type of methods are more commonly known as classifiers. The fundamental difference between these is that in unsupervised methods data is just organized based on its features, simple sorting of numbers being perhaps the simplest unsupervised approach and hierarchical or k-means clustering being the most commonly applied ones. Stratifying cancer diagnostics tests today (e.g. OncotypeDX, MammaPrint, TargetNow) are based on unsupervised methods where a group of pre-defined gene expression values, among other possible sample analysis techniques, are used to diagnose cancer, typically by using a dedicated chip manufactured for that purpose only to measure pre-set 80-100 genes. In supervised methods some machine learning method is used where computer is taught to recognize certain features of the training data and then subsequently it is able to classify novel data based on these features.

In order to better understand significance of an expression profile, a biologically meaningful comparison to known gene expression profiles should be made possible. There are known methods of comparing gene expression samples to each other but usually they fail on either or both of the following: (i) ability to compare single sample against multiple samples (one versus one, or many versus many are more feasible); and (ii) ability to extract biologically sensible information as to which features (=genes) are especially responsible for the found similarity.

Cancer is a very personalized disease on a genetic level. Every cancer is different with enormous number of potential gene mutations and gene expression anomalies—and their combinations across all the approximately 23,000 human genes. It has been shown, e.g. by tumour sequencing projects, that one tumour may have numerous different mutations, and that the same cancer type (like breast cancer, prostate cancer) may have significantly different genetic profiles between individuals.

Currently, cancer diagnostics is done by pathologists performing visual inspection of the histology of the biopsy. Even though this is an indispensable part of the diagnostic procedure it is subject to errors and in some cases visual features cannot reveal the exact nature of the cancer. More advanced methods are based on measuring pre-determined genes that are identified from prior research, and prescribing medication to diagnoses derived from those specific genes.

One problem with the current diagnostic methodologies is that, e.g. because of omitting a number of genes from the scope of the method, they lose information that may be needed for diagnostic and treatment decisions and may even cause a wrong diagnosis if wrong genes are measured. As a result, the diagnostics process is inefficient and may produce only partial, or even wrong, results.

One further problem with the current diagnostic methodologies is that they are not particularly suitable for identifying a primary tumour of a metastasized cancer disease.

PCT application WO2008045389 teaches an improved computerized decision support system and apparatus incorporating bioinformatics software for selecting the optimum treatment for a cancerous condition in a human patient. The system comprises a PCR kit or a gene chip, an integrated detector, a detector for accepting receipt of the gene chip toward analyzing the patient's genotype, a database describing the correlation of patient genotypes and the efficacy and toxicity of various anti-cancer drugs used in treating patients with a particular cancerous condition and a computerized decision support system.

PCT application WO2009131710 teaches a method for identifying genomic signatures linked to survival specific for a disease. The method comprises performing data analysis comprising bioinformatics and computational methodology to identify copy number abnormalities and altered expression of disease candidate genes.

PCT application WO2006135904 teaches a method for producing an improved gene expression profile (GEP) for one or more cell samples. The method involves determining one or more particular gene (PG) improved results (IR) for the cell sample, and compiling the PG IR values to produce one or more forms of improved GEP for the cell sample.

PCT application WO2007137187 teaches a method involving performing a test for a gene and a test for a gene expressed protein from a biological sample of a diseased individual. A determination is made to detect which genes and/or gene expressed proteins exhibit a change in expression compared to a reference. A drug therapy used to interact with the genes and/or gene expressed proteins that exhibited a change in expression that is not single disease restricted, is identified from an automated review of an extensive literature database and data generated from clinical trials.

PCT application WO2009132928 teaches a method for predicting an outcome of a patient suffering from or at risk of developing a neoplastic disease. The method comprises the steps of quantifiably determining the gene expression levels of genes, thus obtaining a pattern of expression levels of the genes, comparing the pattern of expression levels with known, pre-defined reference patterns of expression levels indicative of the outcomes and predicting an outcome of a patient from the comparison using a mathematical function to determine the similarity of the pattern of expression levels with the first reference pattern and the second reference pattern. The method depends on disease candidate genes as the starting point of forming the prediction.

PCT Application WO2009125065 teaches a computer-implemented method for correcting data sets from measurements of properties of biological samples. The method comprises the steps of determining first and second property-specific distribution parameters for each property, determining a property-specific correction element for each version of the parallel measurement device based on the discrepancy between the property-specific distribution parameters, correcting the property value and outputting the property's corrected property value to a physical memory and/or display.

PCT Application WO2008066596 discloses a gene expression barcode for normal and diseased tissue classification. The computer-based method includes the steps of determining threshold of active gene expression across a collection of reference categories each consisting of a plurality of samples. The gene specific thresholds are then used to characterize which genes are in active or inactive states in each of the reference categories. These are defined as the gene expression barcodes of the reference categories. The method is unable to identify genes, which are the most significant ones in the process of identifying a tissue type. The method merely identifies genes whose expression level exceeds a threshold value for the gene. The number of those genes may be very high, making the interpretation of the result very difficult and deteriorates the reliability of the result. Additionally, the method relies on the predefined set of genes, the barcode, for tissue classification. Overall the method assumes each gene to have only two informative expression states, which further limits the predictive potential of the method.

None of the methods known in the art teach a way to analyse and characterize a tissue without first making some assumption about the tissue or limiting the number of genes involved in the process.

OBJECTS OF THE INVENTION

An object of the invention may be to compare in a comprehensive manner an encompassing measurement of a number of related quantifiable biological entities of a case sample, e.g. gene expression information for a multitude of genes from a microarray experiment, to a preferably large collection of comparable reference data and to identify for each reference data category, e.g. tissue, the level of similarity between the case sample and the reference categories per measured biological entity and any and all combinations of the entities.

Another object of the invention may be to provide more comprehensive diagnosis of a disease, e.g. cancer, by identifying a group of reference patients from a reference database based on the similarities between the measurement profile of the patient and the measurement profiles of the reference database.

Yet another object may be to provide a method for diagnostic microarray analysis from a single cancer patient and compare it to data from other normal and cancer tissue samples, in order to provide a detailed diagnostic interpretation of the case sample.

A further possible object of the present invention may be to teach a method, that is based on utilization of supervised clustering, which method allows easy and biologically sensible extraction of data entities (=genes) responsible for the result.

Still another possible object of the method may be to identify the gradual changes in the measurable entities that occur during the time between sample extractions from a single source, usually referred to as a time course experiment.

Yet another possible object of the method may be to identify the biological developmental stage of the case sample, such as happens during the differentiation of tissues, cancer progression, senescence etc.

Another further possible object of the method may be to identify entities, e.g. genes, whose particular quantitative level, e.g. expression level, is unique to a sample category, such as genes with a tissue specific expression level. Those entities may be used to identify category-specific biomarkers or drug target candidates.

BRIEF DESCRIPTION OF THE INVENTION

The invention relates to analysis method of comparing single sample against reference database of samples in order to understand and interpret the biological or medical information of the single sample for both biological- or medical research, diagnosis and therapy. The sample(s) and the reference database may be derived from measurement of any quantifiable biological entities of the biological sample(s). An illustrative but non-restrictive list of such biological entities includes genes, splice variants of genes, micro-RNAs and other types of ribo- or deoxyribonucleic acid sequence combinations, proteins, any quantifiable stages, modifications, conformations or combinations of proteins, sugars, lipids, and any metabolites derived from any biochemical reactions. In order to keep the description compact and understandable, embodiments will be described which relate to comparing single microarray measurement relating to gene expression against a reference database of gene expression measurements, but the embodiments and techniques described herein are applicable to comparing sample of any of the above mentioned quantifiable biological entities against the reference database of comparable samples.

The present invention discloses a method for aligning and quantitatively comparing new microarray data (test sample, query sample) against reference gene expression profiles from a large collection of e.g. healthy and pathological in vivo and/or in vitro samples. In an embodiment, the method compares expression profiles of the test samples with those in the reference data and returns the likelihood of the profile representing each of the known reference data categories as well as the sets of genes that define such similarities. In one preferred embodiment of the invention where gene expression sample(s) are aligned against comparable reference database the method is referred to as Alignment of Gene Expression Profiles (AGEP). It may be useful for the classification of microarray data from different healthy and disease tissue types as well as quantification of cell differentiation states.

The first aspect of the invention is a computer executable method for characterizing, utilizing a reference database, a query sample tissue based on the gene expression data of the tissue. The method may be characterized in that it comprises e.g. the steps of calculating for the genes of the query sample tissue and for a plurality of tissue categories in the reference database an expression match score indicating the likelihood of having the gene expression level observed in the query sample in each of the tissue categories of the reference database, calculating for the genes of the sample tissue and for a plurality of tissue categories of the reference database, using the expression match score, a tissue specificity score that expresses how uniquely a gene identifies the query sample as belonging to the tissue category, calculating, using the tissue specificity score, a tissue similarity score that indicates the overall similarity of the sample tissue in relation to a tissue category of the reference database, and storing at least some resulting characterization data comprising at least one identified tissue category identified using the tissue similarity score and/or at least one gene identified using the high tissue specificity score to a memory device or outputting the data to an output device of a computer.

In an embodiment, the method comprises also the step of transforming the expression profile of the query sample into a format compatible with the reference data.

In an embodiment, the method comprises the step of building expression level density estimates for each gene of a tissue category of the reference database.

In an embodiment, the step of calculating the expression match of a gene of the query sample vis-à-vis a tissue category in a reference database comprises the steps of aligning data from the query sample with the density estimate for that same gene in the tissue category, comparing the expression value of the gene in the query sample to the density estimate and identifying a corresponding density value for the gene of the query sample, and calculating the expression match to be the fraction of evaluation points having density lower than the density of the query sample.

In an embodiment, the calculation of the tissue specificity score of a gene comprises the steps of: calculating ratio-weighted difference values of a plurality of pairs of expression match scores, of which scores one represents the expression match score for the gene in the query tissue and the other one represents the expression match score for the same gene in a tissue other than the query tissue, and calculating the tissue specificity score to be the mean of the ratio-weighted difference values.

In an embodiment, the tissue similarity score is calculated to be the mean of the tissue specificity scores of the genes of the query tissue vis-à-vis a tissue category.

In an embodiment, the method comprises the step of characterizing the query sample using the categorization data the at least one identified tissue category of the reference database.

In an embodiment, the method also comprises the steps of identifying at least one reference patient based on the identified tissue category, and performing, based on the properties of the at least one reference patient, at least the of the following: establishing a diagnosis of the disease, recommending a medication for the disease, and estimating clinical outcomes with a suggested medication.

The properties of the reference patient may comprise e.g. the annotation data of the tissue sample originating from the reference patient.

In a preferred embodiment, the similarity of genetic information, e.g. expression patterns, between the patient and patients of the reference database is determined in a dynamic manner. For example, the similarity of expression patterns may be determined based on genes identified using at least one of the following or their functional equivalents: the em-score and the ts-score.

The diagnosis may be performed without advance knowledge about the identity of any particular gene of the tissue. In other words, knowledge about any pre-defined "candidate genes", "control genes", "housekeeping genes" or "important genes" or any pre-defined "cut-off" value for an expression of a gene, which are identified by e.g. the research community and which are known to contribute to a disease, is not necessarily needed for the diagnosis. Consequently, a tissue may be identified and characterized without any advance knowledge or assumptions about the tissue. For example, no advance assumption is required about possible type of cancer when analysing a cancer tissue. The tissue characterization method of an embodiment is able to find, with a good probability, the right reference tissue categories that together may characterize e.g. the biological properties and behaviour of the query sample. The annotation information of the matching tissues may comprise information e.g. about the probable biological properties and behaviour of the tissue, effective treatments and medications and probable outcome of the treatment.

The known properties of the matching categories may thus provide a foundation for e.g. diagnosis, treatment recommendations and prognosis of a disease, e.g. cancer.

The inventors speculate that a proper diagnosis may be possible even in cases where the exact disease is not yet known e.g. in the research community. Because the method is able to identify on one hand (in a multi-modal manner) a plurality of tissue categories with which the sample tissue has significant similarity and on the other hand the genes significantly contributing to the similarity, valuable information about the important properties, like various aspects about the biological properties and behaviour of the tissue, may be obtained from a plurality of matching tissue categories even if the patient's tissue resembles no tissue category representing a known disease.

The expression match score and/or tissue specificity score may be calculated for at least one, preferably a plurality, most preferably at least 70%, 80%, 90%, 95% or essentially all of the genes of the sample tissue.

In an embodiment, the expression match score (em-score) describes the likelihood of obtaining a worse matching expression for the gene within a tissue category than the one in input sample. More generally, the em-score expresses similarity between an expression value of a sample tissue and a plurality of reference tissues in a manner that is independent from any external context, e.g. from the measurement scales of expression values used.

In an embodiment, the ts-score expresses how uniquely a gene identifies the query sample as belonging to a certain reference data category, e.g. tissue category.

A tissue of the reference database may belong to at least one tissue category. In an embodiment, a tissue belongs to a plurality of tissue categories.

Tissue categories may be formed e.g. using the annotation data of the tissue samples of the reference database. A tissue category may thus represent at least one, preferably a plurality of tissues having a feature described by the annotation data. A tissue may be annotated using any number of annotation data items and it may thus belong to any number of categories.

Tissue specificity scores (ts-scores) for each gene from the test sample for each tissue in the reference database may be calculated from the em-score matrix.

Ts-scores may range e.g. from −1 to 1 and express how uniquely a gene identifies the test sample as belonging to a certain tissue category. Similarity of the input sample at the level of tissues is calculated from tissue specificity scores, resulting in one tissue similarity score per each tissue category.

The tissue similarity score may be specific to a tissue category for example. The tissue may thus have at least one biological property or behaviour particular, typical or possible to the category. For example, a high tissue similarity score of sample tissue A in relation to category X of the reference database may indicate that the sample tissue A may, at least with some probability, have a property particular, typical or possible to tissues of category X.

The characterization of a tissue sample may be performed in a multi-modal manner utilizing the properties of at least one tissue category, preferably a plurality of tissue categories, of a reference database.

An embodiment of an aspect of the present invention may be used for identifying tissue specific genes, i.e. genes whose properties, e.g. expression levels, best characterize a tissue. For this purpose, the uniqueness of the measurable activity of a single measurable entity, e.g. gene expression level, with regards to a single category in any categorization may be calculated e.g. by subtracting the maximum of the density estimates in each evaluation point for the entity in other categories from the density estimate of the entity in the category under study. This results in a number between 0 and 1, which tells us how big a proportion of the observed (measured) quantity of the entity is unique to the category.

A (reference) tissue category may comprise information of at least one tissue. Preferably, a tissue category comprises information about a plurality of tissues having some common aspect or feature. The common aspect or feature may be described using the annotation data of the tissue samples of the reference database.

Any of the methods mentioned herein may utilize a reference database that comprises gene expression activity level estimates, where each estimate describes the distribution of expression levels of a specific gene in a specific tissue category of the reference database.

The tissue characterization data may be used for e.g. providing information suitable for diagnostics purposes, e.g. for determining the type of a cancer, clinical outcomes of the sample patient and best-matching treatments.

The tissue categorization data and/or the tissue annotation data may comprise e.g. any of the following: diagnostic classification data, e.g. information about the type and/or subtype of cancer, type of illness other than cancer, tissue type information, data about observed biological properties or behaviour of the tissue, e.g. epigenetic status or a pathologist's statement, information about the origin, e.g. a patient, of the tissue. The information about the origin may comprise e.g. any of the following: age, sex and ethnicity of the patient, species from which the sample was obtained from, a symptom of the patient, a diagnosis of the patient, medication of the patient, predicted clinical outcome of the patient, actual clinical outcome of the patient, progress of a disease of the patient. Any of the abovementioned data may be associated with in vitro grown samples as well as samples derived by biopsy, purification or any other method of biological sample extraction.

Suitably, the categorization of tissue data may be multi-modal categorization.

An aspect of the present invention may be a computer executable method suitable for e.g. providing a diagnosis for a patient. The method may comprise any, any combination or all of the steps of:

forming, using an embodiment of the method of the present invention, a first reference group by identifying a plurality of patients from a reference database using gene expression data of a first tissue sample, forming, using an embodiment of the present invention a second reference group, by identifying a plurality of patients from a reference database using gene expression data a second tissue sample of the patient, forming a third reference group from the first and the second reference group, identifying clinical outcomes of the formed third reference group, possibly with medications; and providing treatment and/or medication suggestions and/or recovery prognosis based on the information of the third reference group.

The first tissue sample may be e.g. of a cancer tissue. The second tissue sample may be e.g. of a healthy tissue.

Forming additional reference groups e.g. by combining existing reference groups may allow alignment and analysis of the query sample against all possible combinations of categorization of the reference data collection. For example, forming a category by combining all categories of cancers forming a metastasis and the subsequent alignment of the query sample against all categories may allow interpretation of the query sample's profile that it resembles more metastatic cancers in general than any particular cancer type. This may indicate, for example, that the sample is particularly anaplastic and dedifferentiated and the patient has high risk of developing metastatic disease. Categories formed from existing categories can be utilized in all aspects of the invention.

An aspect of the present invention may be a method of building a reference database comprising gene expression data for the purpose of characterizing a test sample tissue. The method may comprise any, any combination or all of the steps of:

importing gene expression data of a plurality of tissue samples into the database, integrating and normalizing the data e.g. for enabling mutual comparison of data, annotating the gene expression data of the tissue sample using at least one tissue categorization data item, calculating an activity level estimate for each gene of each tissue category, where each estimate describes the distribution of expression levels of a specific gene in a specific tissue category of the reference database, e.g. by using any method that is positively influenced by the possible multimodality of the expression within the category, calculating the modality of each gene in each tissue category to provide further categorization.

The accuracy of the annotation of the reference database may be estimated and/or enhanced by characterizing each tissue of the reference database utilizing e.g. the method of the first aspect of the present invention. The accuracy of the annotation may be thus confirmed by the tissue similarity score calculated for a query sample vis-à-vis a tissue category in a reference category.

The annotation data of the gene expression data (and thus also the data usable for tissue categorization) may comprise e.g. any of the following:
- Anatomical and/or histological location from which the sample was obtained
- Pathological status of the tissue from which the sample was obtained
- Complete or any part of the patient's epicrisis
- Results of any medical diagnostics performed on the patient
- Age, gender and ethnicity of the patient
- Species from which the sample was obtained from
- Results of any other measurements/diagnostics/analysis performed from the same sample or comparable sample (e.g. pathologists evaluation of the histology of the sample)
- Lifestyle information, e.g. eating habits, activity level, sleep patterns
- Genetic or epigenetic status of the sample's genome
- Any above mentioned annotation information may also be associated with sample derived from in vitro growing/purification of the original sample obtained from the patient The gene expression data of a tissue sample may comprise expression level information of at least 10000, 15000, 20000, 22000 genes. Preferably, but not necessarily, the expression data comprises the expression level information essentially about the entire genome, e.g. human genome, e.g. at least 95%, 98% or 99% of the genes. Broad coverage of genome is preferred over limited coverage as one of the ideas behind the invention is the principle of not excluding any genes from the analysis on a pre-determined basis. The method will identify for each analysis which genes are probably meaningful for each tissue characterization and which probably are not.

An aspect of the invention may be any computer arrangement comprising means for performing any step, any combination of the steps or all of the steps of any of the methods mentioned herein.

An aspect of the invention may be any computer program product comprising computer executable instructions for performing any step, any combination of the steps or all of the steps of any of the methods mentioned herein.

An aspect of the present invention may be a computer readable memory medium comprising the reference database.

Some aspects of the invention may be suitable for identifying the primary tumor of a patient based on the expression profile of the analysed (metastatized) tumor. For example, a tumor tissue sample taken from liver may exhibit similar expression profile and/or tissue similarity of a pancreatic cancer tissue. Thus, the primary tumor of the cancer may be suspected to reside in pancreas.

DETAILED DESCRIPTION OF PREFERRED EMBODIMENTS

Figure 1B:
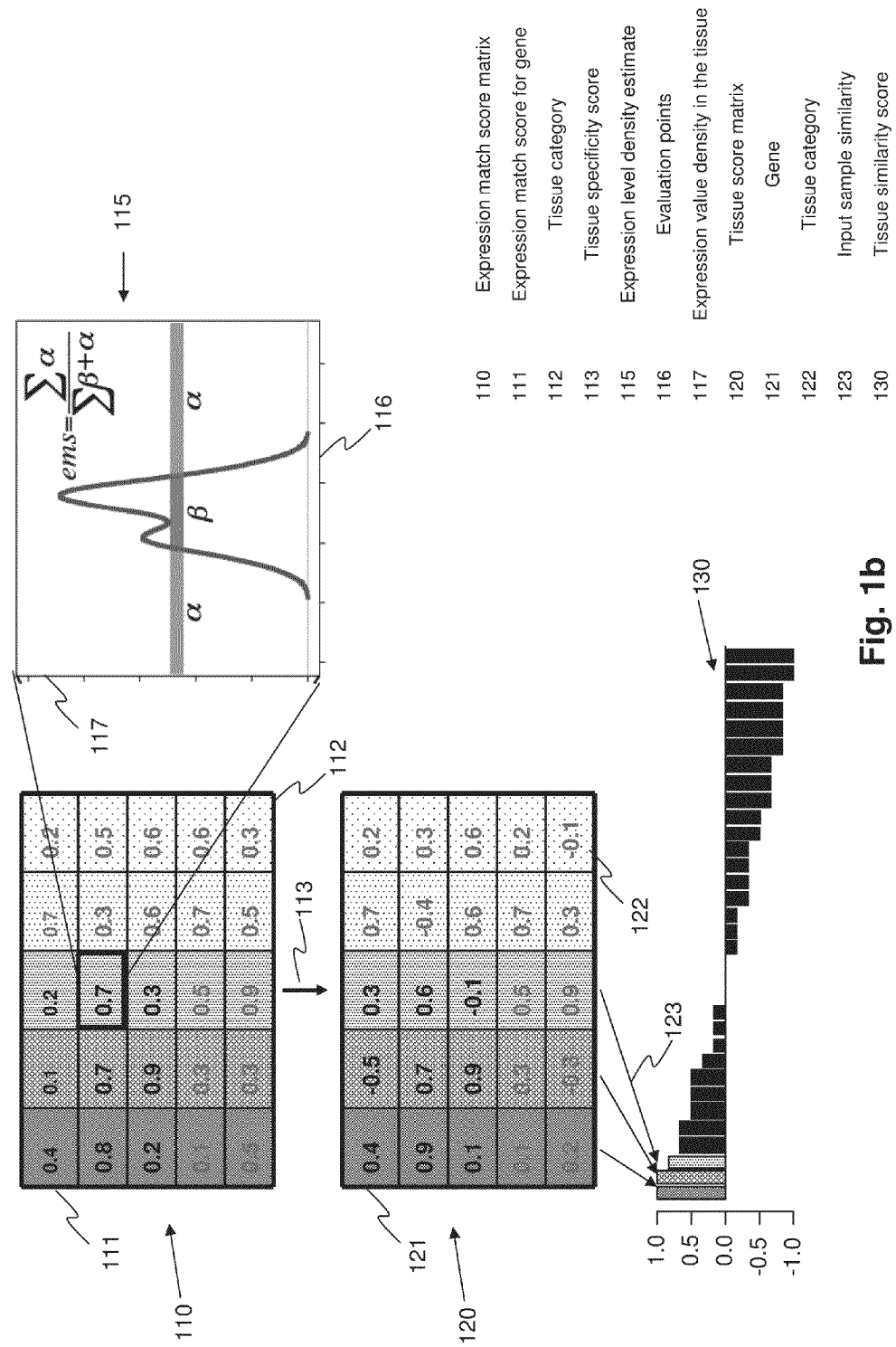
Figure 2A:
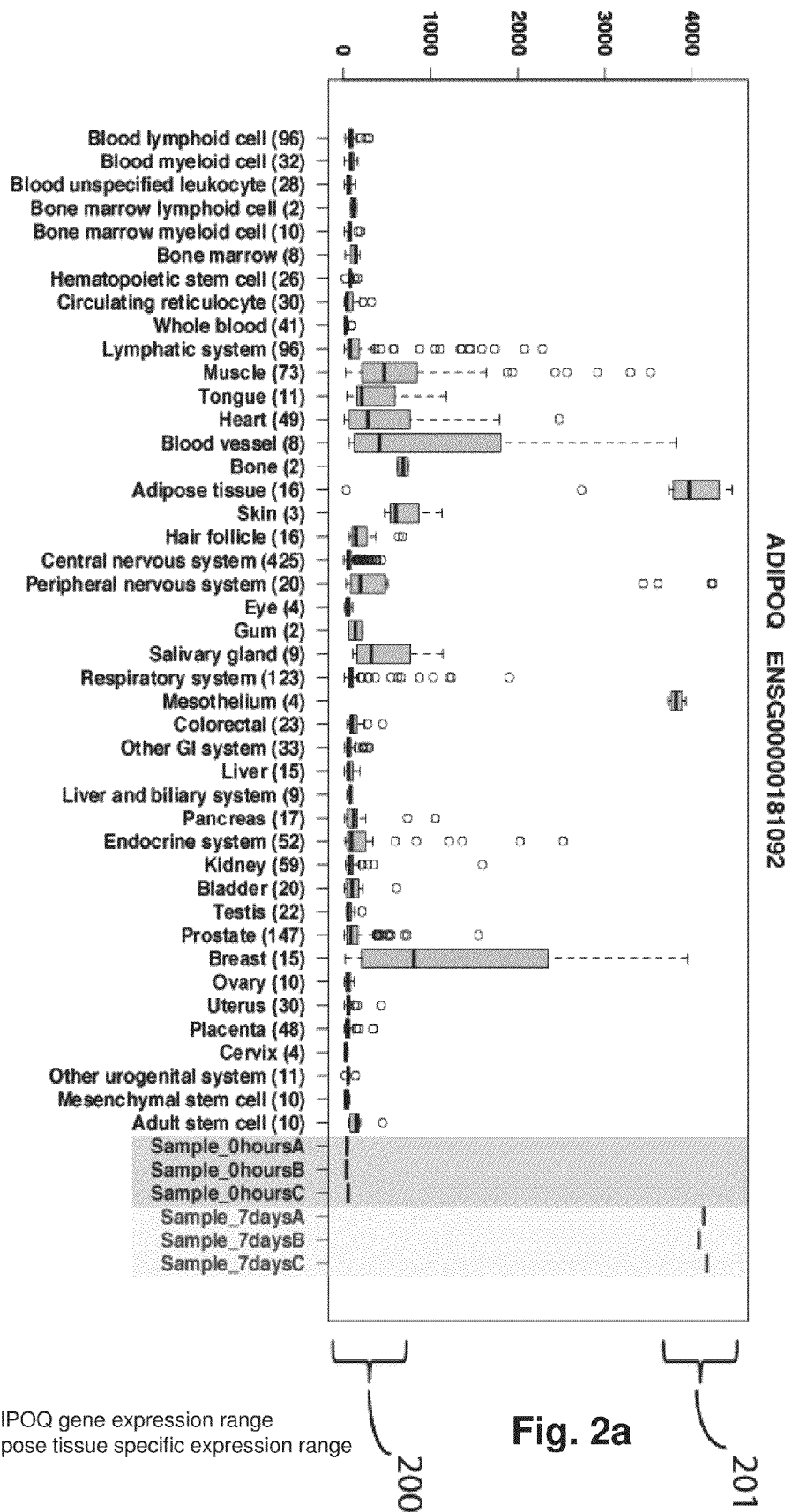
Figure 2B:
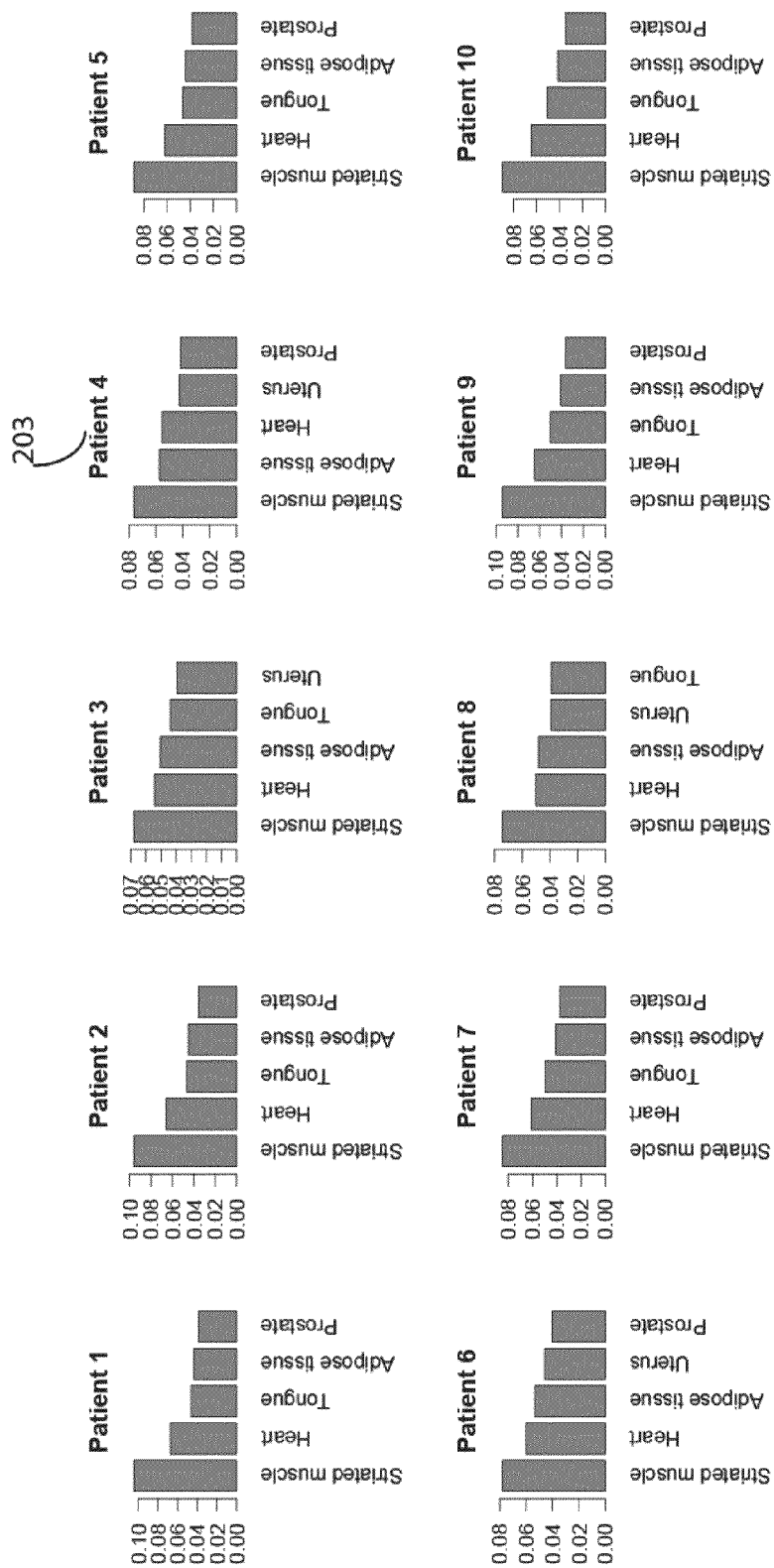

In the following, the invention is described in greater detail with reference to the accompanying drawings in which:

FIG. 1a shows a tissue sample and a reference database comprising data of a plurality of tissue samples, FIG. 1b illustrates the method of a preferred embodiment, FIG. 2a shows the expression profile of ADIPOQ, a known adipose tissue specific gene, across the reference data, samples from the beginning of the time series (0 h samples) and samples from the end of the time series (7 d samples); and FIG. 2b shows alignment results of ten Duchenne Muscular Dystrophy (DMD) patient samples to five most matching reference tissues.

It is reasonable to presume that each human gene has a characteristic expression level in any given tissue type, but the variation in biological tissues guarantees that there are no two absolutely similar biological samples even though they are of the same tissue type. This might cause samples of the same tissue type to have more than one characteristic expression level for a gene. In other words genes can have bi- or multi-modal expression distribution in a tissue. Any selection of single statistical representative value, like mean or median, to reflect the expression level of this kind of gene fails to capture this multimodal distribution and gives an incorrect expression level as the characteristic expression level for the gene.

With enough measurements for each gene in each tissue type it is possible to define which expression levels are characteristics for each gene in each tissue type. Such definition may be e.g. achieved by building, using e.g. kernel density with Gaussian window, expression level density estimates (activity level estimates) for each gene in a plurality of tissue categories. These expression density estimates are then used to align a single query sample profile to the reference database and identify which genes of the query profile have expression levels that resemble expression states of which tissue types (categories).

Another aspect of the invention in this embodiment is the ability of the method to define the similarity of the query sample and reference data tissue categories in terms of likelihood of having expression level observed (in the query sample) in the reference data categories. Gene expression levels are relative values, which are not directly interpretable in terms of biological significance even in the rare case where reference point is absolutely known. Thus, any attempt to describe similarity between two gene expression values by using conventional distance metrics (e.g. Euclidean distance) provide value which is at least equally difficult to interpret in biological significance as are the original values (with the considerably rare exception of difference being equal to zero). A preferred embodiment of the present invention circumvents this problem by providing similarity measure, which is more biologically interpretable as it describes the likelihood of having the observed expression level in the reference tissue category. Thus, the similarity measure of an embodiment of the present invention is independent of any external context, e.g. the measurement scale of gene expression values.

FIGS. 1a and 1b depict the principle of the AGEP method which is one preferred embodiment of the present invention. In the method, microarray data from one test sample 100 (query sample) is compared to samples 103a-i of a large reference database 101 of different tissue/cell types (categories) 102a-c. There are thus, for example, a plurality of tissue samples 103a-c belonging to a tissue category 102a (and 103d-f belonging to category 102b and 103g-i belonging to category 102c). It should be noted that a tissue sample of the reference database may belong to a plurality of categories. This makes the multi-modal similarity analysis of a tissue sample possible.

"Large" here means a database that contains expression data of e.g. at least 100, 1000 or 10000 tissue samples.

A generalized workflow of the AGEP process comprises the following steps.

First, the expression profile of a test sample is first transformed into a format compatible with reference data. Such normalization methods are known to a person skilled in the art. One example about a suitable method is provided in WO2009125065.

Moving to FIG. 1b, the expression level density estimates 115 have been pre-calculated for each gene in each reference tissue category. Then, each gene's data from the test sample is aligned with the density estimate for that same gene in each reference tissue as follows: density of expression values (y-axis 117) in the tissue is estimated in 512 evaluation points (x-axis 116) between the minimum and maximum (in all tissues) expression levels of the gene. The expression value of the gene in the test sample is then compared to the density estimate and a corresponding density value (y-axis 117) is identified. The fraction of evaluation points having lower density ($\alpha$) forms the expression match score (em-score), describing the likelihood of obtaining a worse matching expression for the gene than the one in input sample. The em-score matrix 110 contains an em-score value for each gene 111 of each tissue category 112. An em-score of 1 means that the gene in the input sample had the best matching expression level for the tissue in question, in other words expression of the input sample matched the highest density peak. An em-score of 0 on the other hand means that input sample had an expression level that did not match the tissue at all. This operation is then repeated for all genes of the input sample against all reference tissue categories. Next, tissue specificity scores (ts-scores) for each gene from the test sample for each tissue in the reference database are calculated 113 from the em-score matrix 110. This calculation results as the ts-score matrix 120 which also has a value for each tissue 122 category and gene 121. Ts-scores range from −1 to 1 and tell us how uniquely a gene identifies the test sample as belonging to a certain tissue. Finally, similarity of the input sample at the level of tissues is calculated 123 from tissue specificity scores, resulting in one tissue similarity score 130 per each tissue category of the reference database.

Alignment of a query profile results in a similarity score between the query sample and each of the tissues of the reference data. Behind each of the similarity scores are two scores for each gene. Expression match score (em-score) describes, suitably on the scale of 0 to 1, the likelihood of obtaining less matching expression level for the gene in the particular tissue. In other words, em-score 0 for a gene means that all other expression levels for the gene match better in the particular tissue than the one in query sample. Conversely em-score 1 means that none of the expression levels for the gene match better than the one in query sample.

Genes may be labelled as either "typical" or "atypical" for each tissue. This is done by comparing the query sample's em-score for the gene against the range of em-scores for the same gene gained when the tissue is compared against itself. If the em-score from the comparison is higher than e.g. the lowest 5% from the tissue vs. self-spread, the gene may be termed typical, otherwise it is atypical. This is done because the em-score itself does not tell the spread of expression values a gene has in a tissue. This spread affects the range of expected em-scores when a sample of the tissue is compared against itself. For a gene with a very tight spread, one may expect much higher em-scores than for those with a more loose spread.

Tissue specificity score (ts-score), on the scale of −1 to 1, is further calculated from em-scores to provide insight into whether the gene is expressed at the level unique for the particular tissue. Ts-score 1 for a gene means that the gene has unique expression level on that tissue and in the query sample the expression was on that level. −1 means that the gene has unique expression level but in the query sample expression was not at that level. The mean of the ts-scores of all genes in the particular tissue is used as a similarity score for that tissue.

Together these scores allow biologically meaningful interpretation of the transcriptomic state of the query sample by providing similarity match at the level of tissues, then describing what part of the transcriptome, or in other words which genes, are responsible for the similarity and finally which of the genes are on the level which are specific for the particular tissue.

Expression data to be analyzed against the reference data typically needs to be transformed into compatible form by following procedure using a method known to a person skilled in the art. One such method is taught e.g. in patent publication WO2009125065A1.

The density of expression values of each gene in each tissue type may be calculated e.g. as follows: For computational efficiency fast Fourier transformation may be used based approximation to calculate kernel density estimates. Kernel densities may be calculated by using Gaussian window. Density is estimated from 0 to maximum expression value in the entire dataset with 512 equally spaced points.

The modality of gene expression estimates may be calculated by searching for peaks having at least 0.1 of the total area of the density estimate. Some, preferably low percentage, e.g. 10-20%, of the genes may be excluded from the analysis e.g. due to the ambiguous modality of expression distributions. Modality of the expression profiles of genes can be used to further categorize reference data as well as to assign the query sample into the specific categories based on one or multiple genes.

Gene and tissue specific expression value density estimates are used to calculate likelihood of obtaining expression values observed in a query profile from each tissue type. For a gene g in tissue t this is done as follows:

The value of the density diagram for gene g in tissue t corresponding the expression value of gene g in the query sample is determined. Then that density value is compared to the density values of the 512 evaluation points of the density diagram of gene g in tissue t and the fraction of lower density values is calculated. This is called the expression match score (em-score), with 1 meaning perfect match between the query and tissue for expression of the gene and 0 meaning expression of the gene in the query profile is at non-typical level for tissue. This calculation is repeated for each gene of the query profile against the density estimates of the same genes in each tissue type of the reference data. Additionally, a lower limit for the expected expression match score is calculated for each gene in each tissue type of the reference data to reflect the natural variability of expression of each gene in each tissue. This lower limit may be defined e.g. as the value under which the lowest 5% of em-scores for the gene would settle when a sample from the tissue is compared against itself. The lower limit for the expected expression match score for a gene in a particular tissue is calculated by evaluating the em-scores for all evaluation points, and weighting the abundance of that em-score by the value of the density diagram at that point. The sum of the weights is then normalized to 1. Since the density diagram already represents the levels of gene expression in the tissue, the em-scores, that would be obtained if the corresponding levels of gene expression were compared against the tissue itself, are evaluated. This is repeated for all genes in all tissues. The calculations are detailed in Equation 1:

The distribution of expected em-scores is defined as:

E={evaluation points for gene g in tissue t}

$e_i$=i: th evaluation point n=|E| for each i (1 ... n)

expected em-score=ems($e_{ix}$,t)

with $$weight = \frac{e_{iy}}{\frac{1}{\sum_{i=1}^{n} e_{iy}}}$$

For the purpose of defining the similarity of query sample at the level of tissues, tissue specificity score (ts-score) for each gene in each tissue is calculated as follows (Equation 2):

The tissue specificity score for tissue t and gene g is:

$$tss(t, g) = \frac{1}{n}\sum_{i=1}^{n} f(t, x_i, g)$$

Where

T={non-t tissues} n=|T|

$x_i$=i: th element of T and $$f(t, x, g) = \begin{cases} 1 - 1.25\left(\frac{ems(x, g) + 0.25}{ems(t, g) + 0.25}0.2\right), & \text{for } ems(t, g) > ems(x, g) \\ -\left(1 - 1.25\left(\frac{ems(t, g) + 0.25}{ems(t, g) + 0.25}0.2\right)\right), & \text{for } ems(t, g) < ems(x, g) \end{cases}$$

ems(t, g) = expression match score for tissue t, gene g

The expression match score for the gene g in tissue t and the expression match score for gene g in a tissue other than t is taken, and e.g. 0.25 is added to both numbers. The smaller number is divided by the larger number, resulting in a score between 0.2 and 1. This number is then scaled to range 0-1, and is subtracted from 1. If the expression match score for tissue t was the lower of the two, the score is multiplied by –1. In essence, what this does is give a ratio-weighted difference of the two expression match scores. This calculation is done for all tissue pairs {t, not t}, resulting in n–1 values, where n is the amount of tissues the query sample is compared to. The tissue specificity score for gene g in tissue t is the mean of these values. It varies between 1 and –1 and describes how well gene g classifies the query profile into tissue t. A score of 1 means the gene has a unique level of expression in the tissue and the query profile has expression level matching it perfectly. 0 means that the expression level observed in the query sample cannot differentiate the tissue from other tissues. –1 means gene has a unique level of expression for the tissue and the query profile does not have that specific expression level. The mean of tissue specificity scores is used as similarity score at the tissue level (Equation 3):

The similarity score for sample s and tissue t is:

$$similarity(s, t) = \frac{1}{n}\sum_{i=1}^{n} tss(t, g_i)$$

Where

G={common genes between s and t} n=|G|

$g_i$=i:th element of G

The accuracy of the annotation (e.g. tissue categorization) of the reference database may be validated by e.g. performing a leave-one-out validation by using e.g. a number of healthy samples, e.g. more than 1000 samples, from the reference data. From the results the accuracy of identifying correct tissue type as first hit and distribution of first and secondary hits per each tissue may be calculated. The sensitivity and specificity for each tissue may be calculated as follows: for tissue t true negatives (tn) are non-t tissue samples that match non-t tissues, false negatives (fn) are tissue t samples that match a non-t tissue, true positives (tp) are tissue t samples that matched t and false positives (fp) were non-t tissue samples that matched t. Sensitivity was defined as tp/(tp+fn) and specificity as tn(tn+fp).

In nearest-neighbor classification method the average expression of each gene on each tissue may be calculated to form tissue average profiles. Samples are classified as the tissue having smallest Euclidean distance to the sample in question. A separate classification may be made by classifying samples to the tissue with the highest Pearson correlation coefficient. In all cases, the sample in question is preferably excluded from the calculation of average profiles.

The method disclosed herein provides potentially a number of significant advantages over the solutions of the prior art.

In the art, there is no appropriate simple method for comparing a single gene expression profile against a collection of reference datasets in order to quantify the probability of the match as well as to define readily the nature of the genes defining the similarity. The AGEP method taught herein is based on the use of kernel density with a Gaussian window to build density estimates for expression (activity) levels of each gene across reference sample types that correspond to different normal human tissues. The resulting density estimates make it possible to define which expression levels, or expression states, are characteristic for each gene in each tissue type. The combination of such gene expression density estimates across the genome can then be used to compare gene expression profiles between test and reference samples as well as to identify genes that define such similarities (see e.g. FIG. 1a). It is also possible to take expression data from a single sample, compare it against the reference database and determine its likely identity (such as resemblance to any of the reference tissues) as well as determine the specific genes in the test sample that are characteristics to each of the reference tissue types investigated. The determined "true identity" of the sample may reveal e.g. the primary tumor of a metastasized cancer disease.

The gene and tissue specific density estimates allow defining which expression levels are most characteristic for each gene in each tissue. Some genes may also be observed to have bi- or multimodal distribution even within individual tissues, highlighting the biological variability even in samples from same anatomical/histological annotation and perhaps suggesting different but distinct activity levels for a gene. The essential features of kernel density estimate in characterizing the expression of a gene are its ability to accept multiple expression levels per tissue, and the ability to recognize how narrow or broad these expression levels are. These two attributes are particularly useful when one realizes that all groups (tissues, cell types, etc.) formed from more than one sample are necessarily heterogeneous. If all possible annotation factors were taken into account, each sample would be unique. Also, annotation for some samples may be rather superficial. The kernel density method is capable of handling both these faults and still producing accurate results.

The AGEP method makes it possible to compare a single sample to a reference database in two important ways. First, it is possible to determine how well a gene's expression matches the expression profile of the same gene in all tissues in the reference database. This similarity is quantified by a number, called the expression match score (em-score), ranging from 0 to 1. A score of zero indicates no match, and 1 is a perfect match. At this point it may also be determined if the gene's expression level is typical for each tissue. This is done by comparing the aligned sample's em-score for the gene against the range of expected em-scores gained from comparing the tissue against itself. If the em-score is higher than e.g. the bottom 5% of these expected em-scores, the gene's expression is deemed typical for the tissue and otherwise it is labeled as atypical. Furthermore, we determine tissue specificities for each gene, by calculating the extent to which that gene identifies a sample as belonging to a certain tissue. For example, if a gene is expressed at an ambient, low level in a multitude of tissues, even though in the sample we are aligning its expression level might perfectly match that basal level, the specificity of the gene for any of those tissues is low because the same expression level matches many other tissues. Specificity is given as the tissue specificity score (ts-score), which is calculated by comparing the em-scores of the gene for all tissues. Ts-scores range from −1 to 1, with a negative score meaning that the expression level matches other tissues better than this one, a positive one meaning it matches this tissue better than others. The closer the score is to 1, the more uniquely the gene identifies the sample as belonging to the tissue, and conversely the closer it is to −1, the more it says that the sample most definitely does not belong to this tissue. A score close to zero means the gene's expression value is inconclusive for determining a tissue.

This patent application discloses a new widely applicable method for the alignment of gene expression microarray profiles, in order to study global transcriptomic profiles of individual test samples by comparison with those contained in a large reference database. As the number of microarray experiments in the public domain increases, and their annotation improves, this approach will become more and more powerful and informative. This approach has significant utility in the analysis of tissue/cell type of origin of samples, as well as in the mapping of differentiation-associated gene expression changes e.g. in stem cells.

Most microarray analyses are usually interpreted only in the context of the original study design and the samples available to the investigator at a given time, resulting in most cases in a case vs. control comparison of two groups of samples. In contrast, the AGEP approach provides an opportunity for a multi-modal comparison of test samples with a comprehensive collection of different cell/tissue types previously studied by microarrays by the entire research community. This approach is therefore likely to provide a deeper view with more information content.

Many previously applied statistical methods also restrict the information content in the genome based on an upfront selection of gene sets or diagnostic classifiers. These selected genes are then only informative in the identical study setting and in the case of very defined questions (like diagnostic/prognostic classifiers). AGEP does not depend on any a priori assumptions of subsets of genes being more informative and diagnostic than others, but nevertheless allows analysis of the similarity at any level between tissue and individual genes to facilitate the interpretation of the expression profile of a sample. Additionally, most previous methods for microarray data analysis are not optimally, if at all, suitable for the analysis of microarray data from individual samples. Thus AGEP method is particularly powerful, when a deeper interpretation of microarray results is needed for individual samples for which no specific control tissue is available, cannot be sampled or would not be an appropriate control. While the availability of reference database information may not replace the appropriate control sample in typical case-control studies, it may provide a different angle for data analysis and interpretation of microarray data from many different sample types (e.g. comparisons across different normal tissue/cell types or analyses of stem cells, or cancers whose normal tissue is not available, not known or not informative).

An embodiment of the method of the present invention depends on a kernel density algorithm to assess the similarity of individual samples against a reference database and it can be implemented on any suitable large and integrated reference datasets. Bimodal or even multi-modal distributions of gene expression levels are common in normal, and particularly disease tissues. Due to the common outlier gene profiles in different tissue/cell samples, linear similarity metrics (such as Euclidean distance) often become unreliable. In contrast, AGEP analysis provides biologically significant information as uniquely high or low expression values in a subpopulation of reference samples is taken into account. Furthermore, AGEP may be able to deal with missing values easily, which is not the case for several other methods. AGEP not only provides a metric of the sample similarities, but also defines those specific genes that are informative in comparison to other reference samples. This is important in order to understand the biological basis of the transcriptomic similarities observed.

As illustrated here, the potential applications range from the analysis of tissue specific genes expression to exploration of cell differentiation and cancer. The very basic questions that can be address include: "What tissue type does this profile mostly resemble?", "Which genes are contributing to the similarity to a certain tissue?" or "What biological processes are different in the test sample as compared to the tissue type that it most closely resembles?". These types of questions are difficult to answer without an ability to align expression profile against a large collection of known profiles to dissect the similarities and differences.

To a person skilled in the art, the foregoing exemplary embodiments illustrate the model presented in this application whereby it is possible to design different methods and arrangements, which in obvious ways to the expert, utilize the inventive idea presented in this application.

EXAMPLES

Example 1

Application of the Array Alignment for the Microarray Data Analysis: Stem Cell Differentiation Samples from a differentiation series of mesenchymal stem cells transforming into adipocytes were compared to reference data containing mesenchymal stem cell and adipose tissue samples. It was shown that the method is able to both show progression of differentiation and the genes whose expression level changes with the progression.

Samples were compared to the reference data as per the described method. The changes in the results are highlighted by comparing the samples from the beginning of the time series, the 0 h samples, with the samples from the end of the series, the 7 d samples. First of all, the 0 h samples had mesenchymal stem cells as the tissue they most resembled, whereas the 7 d samples resembled adipose tissue the most. On the level of biological processes composed of several genes, the trend was also very clear. Genes contributing to adipose tissue related processes, such as lipid and fatty acid transport, changed their expression during the time series away from their levels in mesenchymal stem cells to match those of adipose tissue, as determined by relative enrichment of matching genes.

Finally, at the level of individual genes, the change was also readily apparent. Several adipose tissue specific biomarkers, such as the ADIPOQ gene, had a basal expression level in the 0 h samples, common to the majority of tissues, but in the 7 d samples their expression was elevated to adipose tissue specific levels. FIG. 2a, where y-axis shows the expression of ADIPOQ gene across the reference tissues on the x-axis, show how ADIPOQ gene expression change during the differentiation (200) and differentiated stem cells reach the adipose tissue specific expression range (201). While this particular gene is already known to relate adipose tissue differentiation the presented method allows quantification of matching expression levels of all genes against all reference tissues and therefore entirely characterizes changes in the transcriptomic program.

Example 2

Application of the Array Alignment for the Interpretation of Microarray Data: Dystrophic Muscle One purpose of the invention is to provide meaningful interpretation for the gene expression of pathological samples for diagnostic and/or therapeutic purposes. For example when comparing dystrophic muscle samples to healthy striated muscle reference data one can provide molecular level interpretation of the patient. Muscle samples from patients suffering from Duchenne Muscular Dystrophy (DMD) were analyzed, with the reference data containing a large amount of healthy muscle samples.

As shown in FIG. 2b, which shows similarity of the dystrophic muscle samples to five most similar reference tissues, all samples identified healthy muscle as their closest tissue match, but one sample which is associated with Patient 4 (203) identified adipose tissue as second closest match. All samples displayed abnormal, as compared to healthy muscle, expression of genes relating to inflammatory and immune responses, revealing the diseased nature of the samples. Also, at the level of individual genes, the DMD gene, the hallmark of dystrophic muscle, had an expression that greatly deviated from its usual level in healthy muscle.

Interestingly, one sample had adipose tissue as its second match (203). This could be due to the sample being taken from fatty layers, or perhaps is indicative of more advanced state of the disease, as it is common for dystrophic muscle to have more fat tissue replacing its dystrophic muscle tissue. Once again the method demonstrated its power to analyze a sample in detail.

The invention claimed is:

1. A computer executable method for characterizing, utilizing a reference database, a query sample based on the gene expression data of the sample, wherein the method comprises the steps of:
   a. calculating for genes of the query sample and for a plurality of tissue categories in the reference database an expression match score indicating the likelihood of having the gene expression level observed in the query sample in each of the tissue categories of the reference database,
   b. calculating for the genes of the query sample and for the plurality of tissue categories of the reference database, using the expression match score, a tissue specificity score that expresses how uniquely a gene identifies the query sample as belonging to a tissue category,
   c. calculating, using the expression match score or the tissue specificity score, a tissue similarity score that indicates the overall similarity of the query sample in relation to a tissue category of the reference database,
   d. storing at least some resulting characterization data comprising at least one identified tissue category identified using the tissue similarity score and/or at least one gene identified using the tissue specificity score or the expression match score to a memory device or outputting the data to an output device of a computer, and
   e. building expression level density estimates for each gene of a tissue category of the reference database, wherein the step of calculating the expression match score of a gene of the query sample vis-a-vis a tissue category in a reference database comprises the steps of:
   f. aligning data from the query sample with the density estimate for that same gene in the tissue category,
   g. comparing the expression value of the gene in the query sample to the density estimate,
   h. identifying a corresponding density value for the gene of the query sample, and
   i. calculating the expression match score to be the fraction of evaluation points having density lower than the density of the query sample.

2. A method according to claim 1, wherein the method comprises the step of transforming the expression profile of the query sample into a format compatible with the reference data.

3. A method according to claim 1, wherein said tissue similarity score is calculated to be the mean of the tissue specificity scores or mean of the expression match scores of the genes of the query sample vis-a-vis a tissue category.

4. A method according to claim 1, wherein the method comprises the step of characterizing the query sample using the categorization data from at least one identified tissue category of the reference database.

5. A method according to claim 1, wherein the method comprises the steps of:
   a. identifying at least one reference patient based on the identified tissue category, and
   b. performing, based on the properties of the at least one reference patient, at least one of the following:
      i. establishing a diagnosis of the disease,
      ii. recommending a medication for the disease, and
      iii. estimating clinical outcomes with a suggested medication.

6. The method of claim 1, wherein said calculation of the tissue specificity score of a gene comprises the steps of:
   j. calculating ratio-weighted difference values of a plurality of pairs of expression match scores, of which scores one represents the expression match score for the gene in the query tissue and the other one represents the expression match score for the same gene in a tissue other than the query tissue, and k. calculating the mean of the ratio-weighted difference values.

7. A computer arrangement for characterizing, utilizing a reference database, a query sample based on the gene expression data of the sample, wherein the arrangement comprises means for:
   a. calculating for genes of the query sample and for a plurality of tissue categories in the reference database an expression match score indicating the likelihood of having the gene expression level observed in the query sample in each of the tissue categories of the reference database,
   b. calculating for the genes of the query sample and for the plurality of tissue categories of the reference database, using the expression match score, a tissue specificity score that expresses how uniquely a gene identifies the query sample as belonging to a tissue category,
   c. calculating, using the tissue specificity score, a tissue similarity score that indicates the overall similarity of the query sample in relation to a tissue category of the reference database,
   d. storing at least some resulting characterization data comprising at least one identified tissue category identified using the tissue similarity score and/or at least one gene identified using the tissue specificity score or the expression match score to a memory device or outputting the data to an output device of a computer, and
   e. building expression level density estimates for each gene of a tissue category of the reference database, wherein the means for calculating the expression match score of a gene of the query sample vis-a-vis a tissue category in a reference database comprises a means for:
   f. aligning data from the query sample with the density estimate for that same gene in the tissue category,
   g. comparing the expression value of the gene in the query sample to the density estimate,
   h. identifying a corresponding density value for the gene of the query sample, and
   i. calculating the expression match score to be the fraction of evaluation points having density lower than the density of the query sample.

8. The computer arrangement of claim 7, wherein said means for calculating the tissue specificity score of a gene comprises means for:
   j. calculating ratio-weighted difference values of a plurality of pairs of expression match scores, of which scores one represents the expression match score for the gene in the query tissue and the other one represents the expression match score for the same gene in a tissue other than the query tissue, and
   k. calculating the mean of the ratio-weighted difference values.

9. A non-transitory computer readable memory medium for characterizing, utilizing a reference database, a query sample based on the gene expression data of the sample, wherein the non-transitory computer readable memory medium comprises computer executable instructions for:
   a. calculating for genes of the query sample and for a plurality of tissue categories in the reference database an expression match score indicating the likelihood of having the gene expression level observed in the query sample in each of the tissue categories of the reference database,
   b. calculating for the genes of the query sample and for the plurality of tissue categories of the reference database, using the expression match score, a tissue specificity score that expresses how uniquely a gene identifies the query sample as belonging to a tissue category,
   c. calculating, using the tissue specificity score, a tissue similarity score that indicates the overall similarity of the query sample in relation to a tissue category of the reference database,
   d. storing at least some resulting characterization data comprising at least one identified tissue category identified using the tissue similarity score and/or at least one gene identified using the tissue specificity score or the expression match score to a memory device or outputting the data to an output device of a computer, and
   e. building expression level density estimates for each gene of a tissue category of the reference database, wherein the means for calculating the expression match score of a gene of the query sample vis-a-vis a tissue category in a reference database comprises a means for:
   f. aligning data from the query sample with the density estimate for that same gene in the tissue category,
   g. comparing the expression value of the gene in the query sample to the density estimate,
   h. identifying a corresponding density value for the gene of the query sample, and
   i. calculating the expression match score to be the fraction of evaluation points having density lower than the density of the query sample.

10. The non-transitory computer readable memory medium of claim 9, wherein the instructions for calculating the tissue specificity score of a gene comprises instructions for:
   j. calculating ratio-weighted difference values of a plurality of pairs of expression match scores, of which scores one represents the expression match score for the gene in the query tissue and the other one represents the expression match score for the same gene in a tissue other than the query tissue, and
   k. calculating the mean of the ratio-weighted difference values.

\* \* \* \* \*